(12) United States Patent
Fukui et al.

(10) Patent No.: US 11,156,683 B2
(45) Date of Patent: Oct. 26, 2021

(54) STATIC MAGNETIC FIELD ADJUSTMENT DEVICE FOR MAGNETIC RESONANCE IMAGING APPARATUS AND SUPERCONDUCTING MAGNET

(71) Applicant: Mitsubishi Electric Corporation, Tokyo (JP)

(72) Inventors: Hideki Fukui, Tokyo (JP); Tetsuya Matsuda, Tokyo (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 16/636,683

(22) PCT Filed: Oct. 26, 2017

(86) PCT No.: PCT/JP2017/038690
§ 371 (c)(1),
(2) Date: Feb. 5, 2020

(87) PCT Pub. No.: WO2019/082332
PCT Pub. Date: May 2, 2019

(65) Prior Publication Data
US 2020/0264252 A1 Aug. 20, 2020

(51) Int. Cl.
*G01R 33/3873* (2006.01)
*G01R 33/3815* (2006.01)
*A61B 5/055* (2006.01)

(52) U.S. Cl.
CPC ..... *G01R 33/3873* (2013.01); *G01R 33/3815* (2013.01); *A61B 5/055* (2013.01)

(58) Field of Classification Search
USPC ........................................................ 324/322
See application file for complete search history.

(56) References Cited

U.S. PATENT DOCUMENTS

| 5,786,695 A | * | 7/1998 | Amor | .................. | G01R 33/3873 |
| | | | | | 324/319 |
| 10,578,693 B2 | * | 3/2020 | Sakakura | ........... | G01R 33/4215 |

(Continued)

FOREIGN PATENT DOCUMENTS

| JP | H04054938 A | 2/1992 |
| JP | 2008289703 A | 12/2008 |

(Continued)

OTHER PUBLICATIONS

International Search Report (PCT/ISA/210), with translation, and Written Opinion (PCT/ISA/237) dated Nov. 21, 2017, by the Japan Patent Office as the International Searching Authority for International Application No. PCT/JP2017/038690.

(Continued)

*Primary Examiner* — Rodney E Fuller
(74) *Attorney, Agent, or Firm* — Buchanan Ingersoll & Rooney PC

(57) ABSTRACT

A static magnetic field adjustment device for an MRI includes a shim tray, a bottom spacer and a magnetic material shim. The shim tray is mounted on the MRI and provided with a shim pocket. The bottom spacer is made of a non-magnetic material and accommodated in the shim pocket to make contact with a bottom surface of the shim pocket. The magnetic material shim is made of a magnetic material and accommodated in the shim pocket with the bottom spacer interposed between the magnetic material shim and the bottom surface of the shim pocket.

10 Claims, 7 Drawing Sheets

(56) References Cited

U.S. PATENT DOCUMENTS

2008/0169813 A1* 7/2008 Yamashita ......... G01R 33/4215
324/321
2008/0290871 A1 11/2008 Tamura
2011/0006769 A1 1/2011 Iwasa et al.

FOREIGN PATENT DOCUMENTS

JP 2011015840 A 1/2011
JP 2015211766 A 11/2015

OTHER PUBLICATIONS

Notice of Reasons for Refusal dated Apr. 10, 2018, by the Japan Patent Office for Japanese Application No. 2018-509871.

* cited by examiner

1

STATIC MAGNETIC FIELD ADJUSTMENT DEVICE FOR MAGNETIC RESONANCE IMAGING APPARATUS AND SUPERCONDUCTING MAGNET

TECHNICAL FIELD

The present invention relates primarily to a device to adjust a static magnetic field formed in an imaging region of a magnetic resonance imaging apparatus, and a superconducting magnet including this device.

BACKGROUND ART

During installation of a magnetic resonance imaging apparatus (hereinafter called an MRI) using a static magnetic field magnet, adjustment of a static magnetic field (hereinafter called shimming) as described in PTL 1 is performed in order to achieve a highly homogeneous static magnetic field in an imaging region of the MRI. In the shimming, plate-like members having a rectangular shape and made of a magnetic material, which are called shims, are accommodated in a plurality of recesses provided in a tray. The tray having the shims accommodated therein is then mounted on the MRI. As a result, the static magnetic field in the imaging region is adjusted to a level of homogeneity required in the MRI.

CITATION LIST

Patent Literature

PTL 1: Japanese Patent Laying-Open No. 2008-289703

SUMMARY OF INVENTION

Technical Problem

When performing the shimming, effect on the static magnetic field caused by the mounting of the tray having the shims accommodated therein on the MRI, that is, a magnetic field output value, is calculated in advance by a computer or the like. Then, an amount of shims to be actually accommodated in the tray is determined based on a result of this calculation. A problem, however, has been that even if the amount of shims determined based on the result of the calculation is accommodated in the tray, the static magnetic field in the imaging region cannot attain the level of homogeneity required in the MRI, that is, there is a discrepancy between the calculated magnetic field output value and the actual magnetic field output value.

The present invention has been made in view of the above, and an object of the present invention is to provide a static magnetic field adjustment device for an MRI capable of suppressing a discrepancy between a calculated magnetic field output value and an actual magnetic field output value, and a superconducting magnet including this device.

Solution to Problem

To solve the problem and achieve the object described above, a static magnetic field adjustment device for an MRI according to the present invention includes: a shim tray mounted on the MRI and provided with a recess; a bottom spacer made of a non-magnetic material and accommodated in the recess to make contact with a bottom surface of the recess; and a magnetic material shim made of a magnetic material and accommodated in the recess with the bottom spacer interposed between the magnetic material shim and the bottom surface.

Advantageous Effects of Invention

According to the present invention, a discrepancy between a calculated magnetic field output value and an actual magnetic field output value can be suppressed.

DESCRIPTION OF EMBODIMENTS

A static magnetic field adjustment device for an MRI and a superconducting magnet according to one embodiment are described with reference to the attached drawings.

First Embodiment

Figure 1:
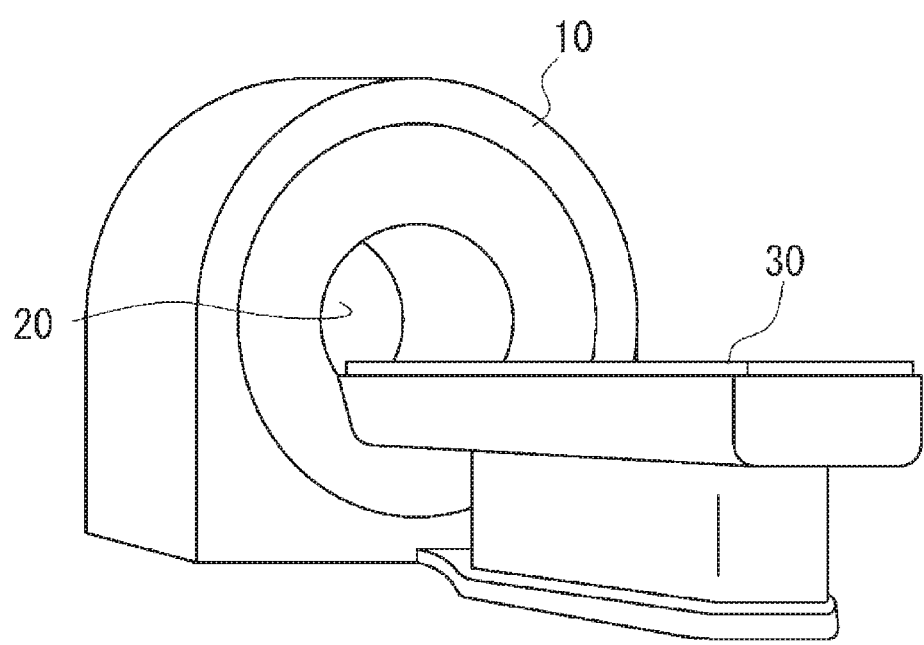
FIG. 1 is a perspective view showing an external appearance of an MRI according to a first embodiment.

FIG. 1 is a perspective view showing an external appearance of an MRI 1. As shown in FIG. 1, MRI 1 includes a static magnetic field generating unit 10 and a bed 30. Static magnetic field generating unit 10 includes a superconducting magnet 100 which will be described later, and generates a static magnetic field in a bore 20.

Figure 2:
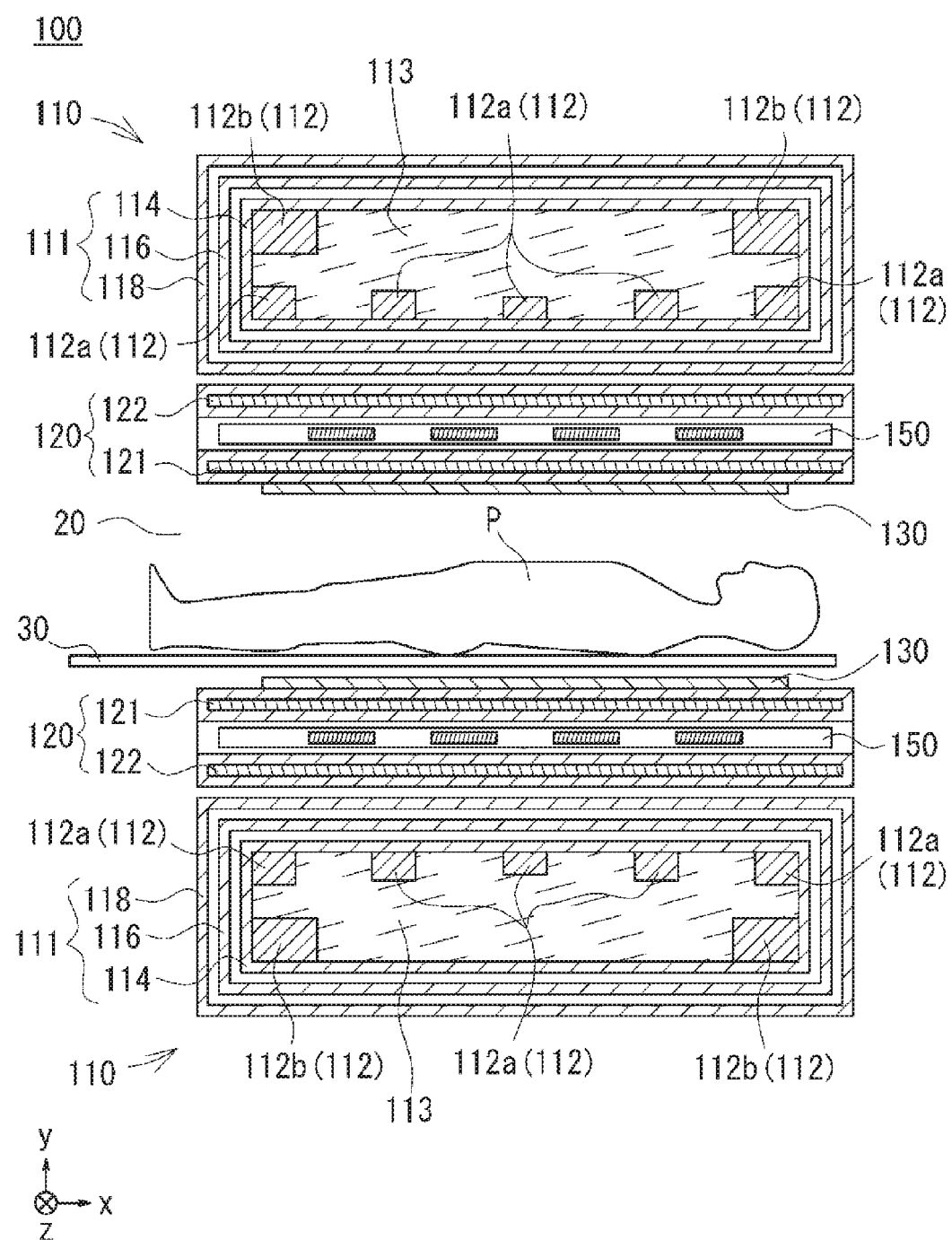
FIG. 2 shows an example of a schematic structure of a superconducting magnet including a static magnetic field adjustment device for an MRI according to the first embodiment.

As shown in FIG. 2, superconducting magnet 100 includes a static magnetic field magnet 110, a gradient coil 120, an RF coil 130, and a static magnetic field adjustment device 150 for an MRI.

Static magnetic field magnet 110 is a magnet having a substantially cylindrical shape, and generates a static magnetic field in a space on the inner side of the cylinder, namely, in bore 20. Static magnetic field magnet 110 is a superconducting magnet, and has a cryogenic container 111, and a superconducting coil 112 immersed in coolant within cryogenic container 111.

Superconducting coil 112 is a coil formed by winding a superconducting wire of NbTi or the like, and is accommodated in cryogenic container 111 together with a liquid helium 113 as a refrigerant required to keep superconducting coil 112 in a superconducting state. Superconducting coil 112 is formed of a static magnetic field main coil 112a to generate a static magnetic field, and a static magnetic field shield coil 112b to suppress leakage of the static magnetic field generated by static magnetic field main coil 112a to the surroundings. Static magnetic field main coil 112a and static magnetic field shield coil 112b each have an annular shape, and have central axes substantially coinciding with each other.

Cryogenic container 111 is formed of a helium cell 114 to accommodate liquid helium 113 and superconducting coil 112, a heat shield 116 for blocking entry of heat from outside, and a vacuum cell 118 to keep the inside of cryogenic container 111 under vacuum. Cryogenic container 111 is normally connected to a refrigerator in order to suppress the consumption of liquid helium 113.

Gradient coil 120 is formed in a substantially cylindrical shape, and disposed on the inner circumferential side of static magnetic field magnet 110. For example, gradient coil 120 is an ASGC (Active Sheilded Gradient Coil), and has a main coil 121 and a shield coil 122. Main coil 121 applies, based on a current supplied from a power source, a gradient magnetic field that varies in strength in directions of x axis, y axis and z axis to a subject P. Shield coil 122 generates a magnetic field on the outer side of main coil 121, to thereby shield the gradient magnetic field generated by main coil 121.

RF coil 130 is formed in a substantially cylindrical shape, and disposed on the inner circumferential side of gradient coil 120. RF coil 130 applies an RF (Radio Frequency) magnetic field to subject P based on an RF pulse. RF coil 130 receives a magnetic resonance signal emitted from subject P by excitation of hydrogen nuclei.

Figure 3:
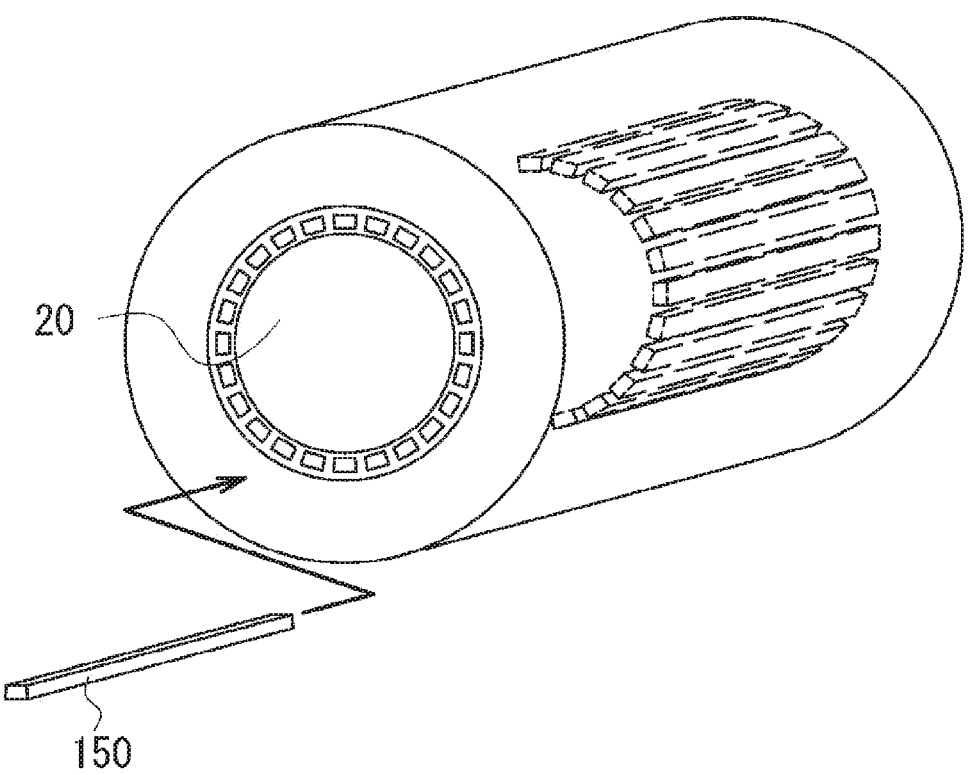
FIG. 3 shows the static magnetic field adjustment device for an MRI according to the first embodiment that has been mounted.
Figure 4:
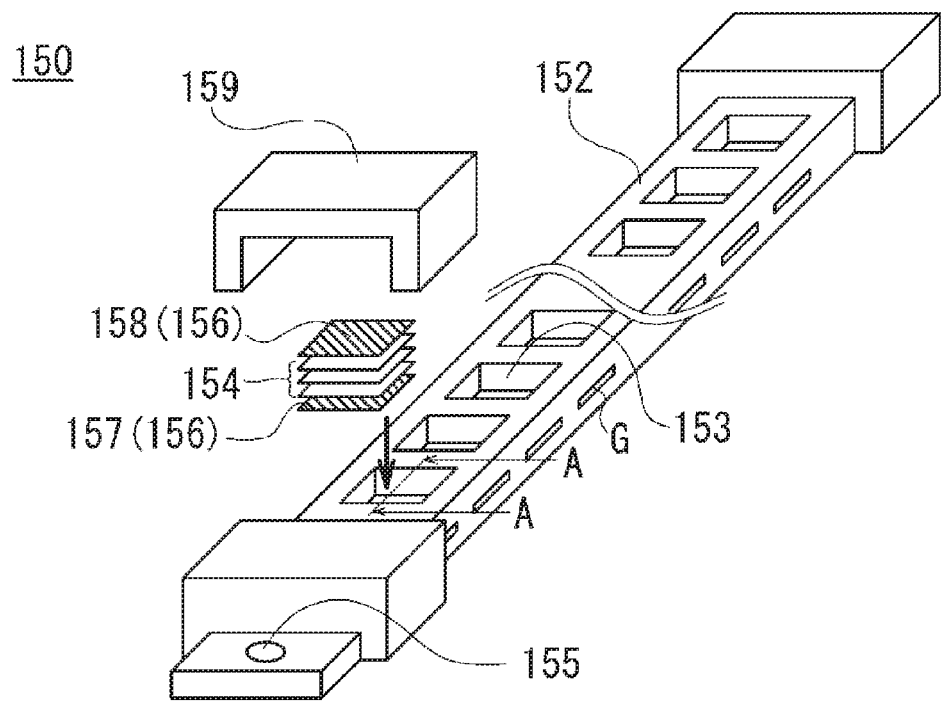
FIG. 4 is a perspective view of the static magnetic field adjustment device for an MRI according to the first embodiment.

Static magnetic field adjustment device 150 for an MRI is mounted on superconducting magnet 100 as shown in FIG. 3, and used to adjust a static magnetic field in an imaging region. Static magnetic field adjustment device 150 for an MRI includes a shim tray 152, magnetic material shims 154, shim spacers 156, and a cover 159, as shown in FIG. 4.

Shim tray 152 is a component substantially in the form of a rectangular parallelepiped made of a non-magnetic material such as glass fiber. As shown in FIG. 3, a plurality of shim trays 152 are arranged at substantially regular intervals on the inner circumferential side of the cylinder formed by superconducting magnet 100, that is, around bore 20. Further, as shown in FIG. 4, shim tray 152 is provided with a plurality of recesses that are aligned in a longitudinal direction of the rectangular parallelepiped formed by shim tray 152. Magnetic material shims 154 which will be described later are accommodated in each of these recesses (hereinafter called shim pocket 153). In the present embodiment, the longitudinal direction of the rectangular parallelepiped formed by shim tray 152 and the central axis of the cylinder formed by superconducting magnet 100 are parallel to each other. A threaded hole 155 for fixing shim tray 152 to superconducting magnet 100 is provided in each end portion of shim tray 152.

Magnetic material shim 154 is a flat plate made of a magnetic material such as iron. As shown in FIG. 4, magnetic material shim 154 forms a rectangular shape having predetermined vertical and horizontal dimensions so as to fit in shim pocket 153. Further, a plurality of types of magnetic material shims 154 having different thicknesses (0.05 mm to 0.35 mm) are prepared. By accommodating these plurality of types of magnetic material shims 154 in various combinations in each shim pocket 153, the amount (thickness) of magnetic material shims 154 disposed in each shim pocket 153 can be adjusted.

Shim spacer 156 is a component in the form of a flat plate made of a non-magnetic material such as Bakelite or PET (polyethylene terephthalate), for filling the remaining space of shim pocket 153 into which magnetic material shims 154 have been placed. As with magnetic material shim 154, shim spacer 156 forms a rectangular shape having predetermined vertical and horizontal dimensions so as to fit in shim pocket 153, and a plurality of types of shim spacers 156 having different thicknesses are prepared. Shim spacers 156 can be divided into a bottom spacer 157 and a top spacer 158. If shim spacer 156 is made of PET, the thickness of shim spacer 156 can be reduced as compared to when it is made of Bakelite.

Figure 5:
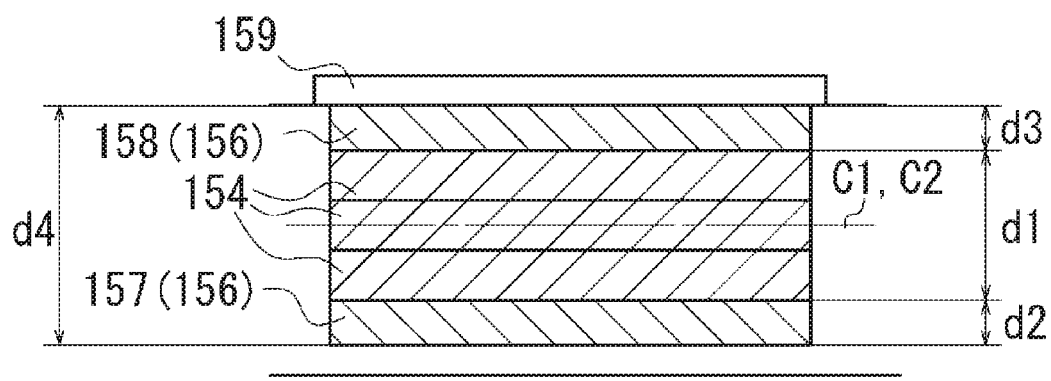
FIG. 5 is a sectional view taken along the line A-A in FIG. 4.

As shown in FIG. 5, bottom spacer 157 is accommodated in shim pocket 153 such that its lower surface makes contact with a bottom surface of shim pocket 153. In the present embodiment, magnetic material shims 154 are disposed to make contact with an upper surface of bottom spacer 157. In other words, magnetic material shims 154 are accommodated in shim pocket 153, with bottom spacer 157 interposed between magnetic material shims 154 and the bottom surface of shim pocket 153. Here, bottom spacer 157 may be formed of a plurality of spacers instead of being formed of a single spacer.

As shown in FIG. 5, top spacer 158 is located opposite bottom spacer 157 with magnetic material shims 154 interposed between them. In other words, top spacer 158 is accommodated in shim pocket 153, with bottom spacer 157 and magnetic material shims 154 interposed between top spacer 158 and the bottom surface of shim pocket 153. Here, a sum of a thickness d1 of magnetic material shims 154, a thickness d2 of bottom spacer 157 and a thickness d3 of top spacer 158 is substantially equal to a depth d4 of shim pocket 153. In the present embodiment, thickness d2 of bottom spacer 157 and thickness d3 of top spacer 158 are substantially equal. As with bottom spacer 157, top spacer 158 may be formed of a plurality of spacers instead of being formed of a single spacer.

As shown in FIG. 4, cover 159 is an snap-type cover that is mounted on shim tray 152, for fixing magnetic material shims 154 and shim spacers 156 accommodated in shim pocket 153. Specifically, cover 159 is a member formed by bending a rectangular flat plate made of a non-magnetic material such as reinforced plastic into a U shape. A hook which is not shown in the figure is provided on each inner side face of the U shape of cover 159. This hook is caught in a groove G formed in each side face of shim tray 152, causing cover 159 to be fixed on shim tray 152. At this time, magnetic material shims 154 and shim spacers 156 in shim pocket 153 covered with cover 159 are also fixed.

Figure 6:
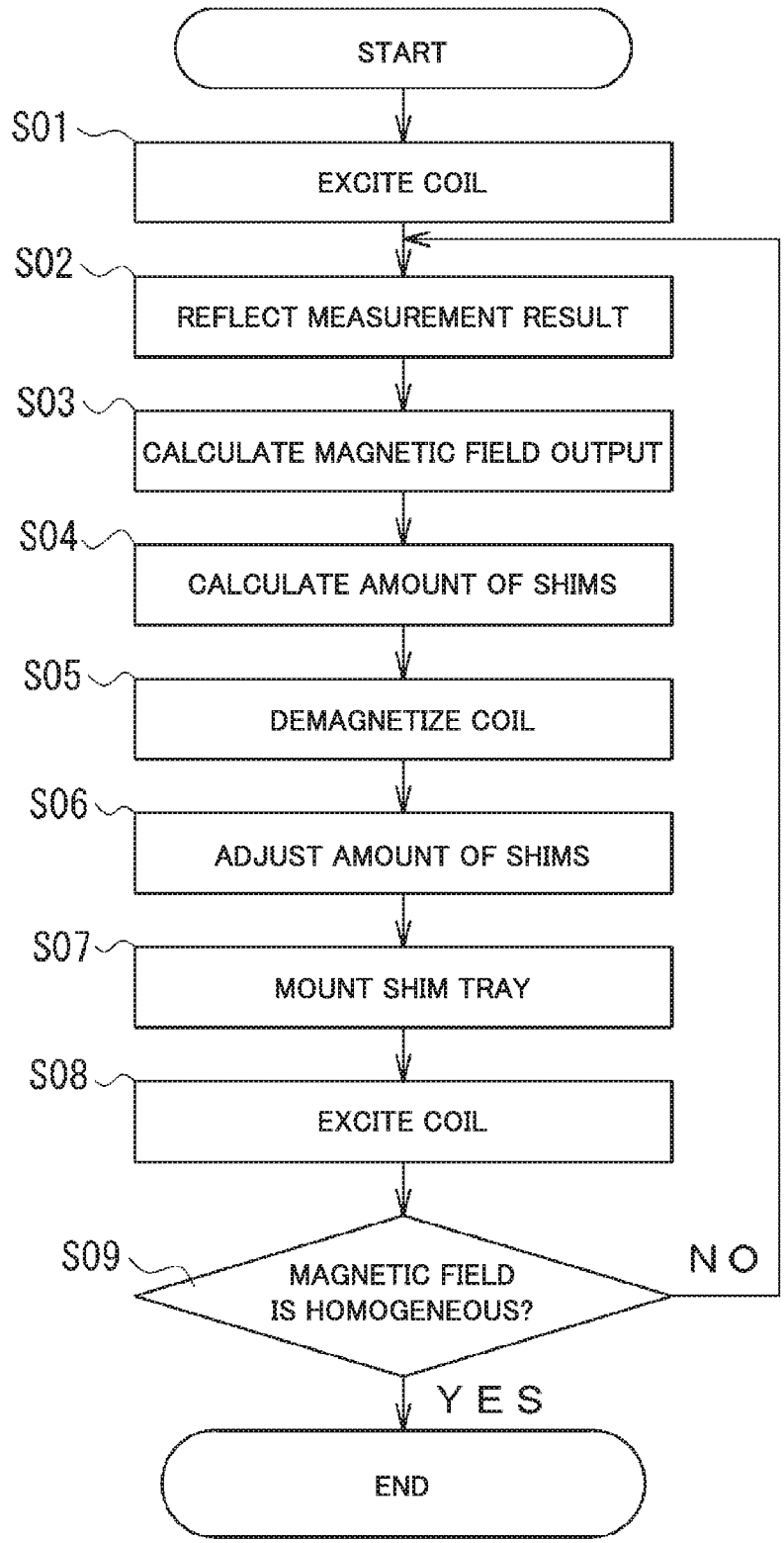
FIG. 6 is a flowchart of shimming.

In the following, shimming with static magnetic field adjustment device 150 for an MRI is described using a flowchart of FIG. 6.

First, superconducting coil 112 is excited without magnetic material shims 154 (with the empty shim tray), to measure the magnetic field in the imaging region. The measurement is conducted at 500 or more points on a surface of the imaging region forming a spherical shape in bore 20 (step S01).

When the measurement is completed, a result of the measurement is reflected in a computer that calculates a magnetic field output value (step S02).

Figure 7:
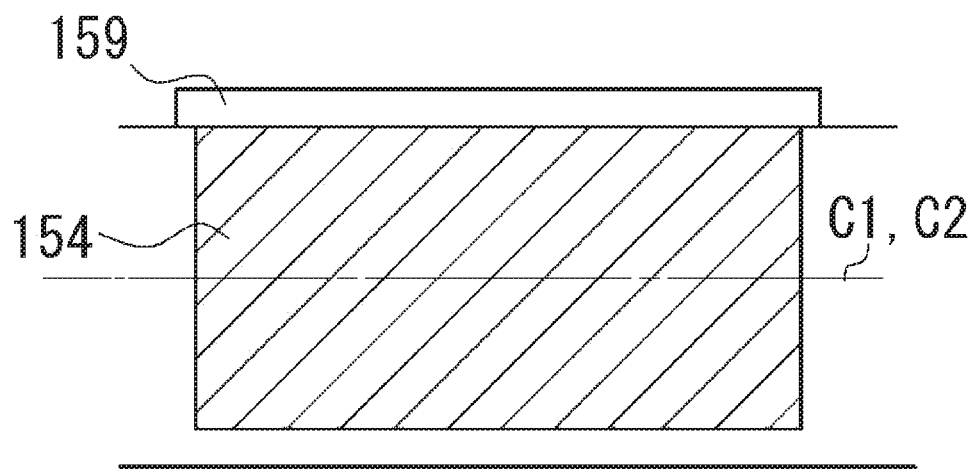
FIG. 7 shows a simulated position of a magnetic material shim in a shim pocket of the static magnetic field adjustment device for an MRI.

Then, the computer reflecting the result of the measurement of the static magnetic field is used to calculate effect on the static magnetic field caused by the accommodation of magnetic material shims 154 in a particular shim pocket 153, that is, a magnetic field output value. Specifically, as shown in FIG. 7, it is assumed that particular shim pocket 153 has been filled with a maximum amount of magnetic material shim 154 that can be accommodated therein. Then, the computer is used to calculate a magnetic field output value when shim pocket 153 has been filled with the maximum amount of magnetic material shim 154 that can be accommodated therein. This calculation is carried out for each shim pocket 153 (step S03).

Based on a result of the calculation described above, a solver is used to calculate an amount of magnetic material shim 154 required for each shim pocket 153 on conditions that the magnetic field in the imaging region becomes homogeneous and a minimum amount of magnetic material shim 154 is used. When calculating the required amount of magnetic material shim 154 by the solver, if the amount of magnetic material shim 154 is half the maximum amount that can be accommodated in shim pocket 153, for example, then the magnetic field output value is proportionally calculated as half the magnetic field output value calculated in step S03 (step S04).

Superconducting coil 112 is temporarily demagnetized, and shim tray 152 is removed from superconducting coil 112 (step S05).

Magnetic material shims 154 having a thickness corresponding to the amount of magnetic material shim 154 calculated in step S04 are inserted into shim pocket 153 of removed shim tray 152. At this time, as shown in FIG. 5, bottom spacer 157 is disposed to make contact with the bottom surface of shim pocket 153, and magnetic material shims 154 are disposed thereon. Further, in order to suppress the movement of magnetic material shims 154 in shim pocket 153, top spacer 158 is disposed on an upper surface side of magnetic material shims 154 as well, and fixed by cover 159 (step S06).

Then, as shown in FIG. 3, shim tray 152 having magnetic material shims 154 inserted therein is mounted on superconducting coil 112 in the demagnetized state (step S07).

Lastly, superconducting coil 112 is excited again (step S08), and the homogeneity of the magnetic field in the imaging region is checked (step S09). The shimming with static magnetic field adjustment device 150 fear an MRI is performed in this manner.

(Effects)

Figure 8:
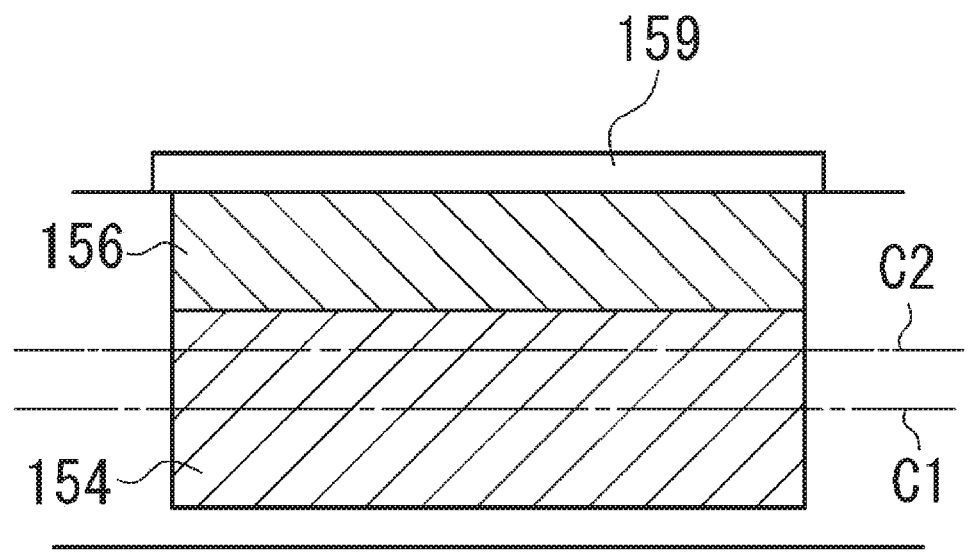
FIG. 8 shows a position of the magnetic material shim in a shim pocket of a conventional static magnetic field adjustment device for an MRI.

In static magnetic field adjustment device 150 for an MRI according to one embodiment, a discrepancy between the calculated magnetic field output value and the actual magnetic field output value can be suppressed. Specifically, as was described in step 03 of the shimming, when calculating the effect on the static magnetic field caused by the insertion of magnetic material shims 154 into particular shim pocket 153, that is, the magnetic field output value, it is assumed that particular shim pocket 153 has been filled with the maximum amount of magnetic material shims 154 that can be accommodated therein. This assumption means that a center C1 in a thickness direction of magnetic material shim 154 is substantially located at a center C2 in a depth direction of shim pocket 153, as shown in FIG. 7. In conventional shimming, in which magnetic material shim 154 is directly placed on the bottom surface of shim pocket 153, as shown in FIG. 8, however, center C1 in the thickness direction of magnetic material shim 154 is not located at center C2 in the depth direction of shim pocket 153. In contrast, in the static magnetic field adjustment device for an MRI according to one embodiment, bottom spacer 157 is placed to make contact with the bottom surface of shim pocket 153, and magnetic material shims 154 are placed thereon, as shown in FIG. 5, so that center C1 of magnetic material shims 154 can be brought closer to center C2 of shim pocket 153. As a result, in static magnetic field adjustment device 150 for an MRI according to one embodiment, the discrepancy between the calculated magnetic field output value and the actual magnetic field output value can be suppressed.

When superconducting coil 112 is in an excited state, a strong electromagnetic attractive force is generated on magnetic material shims 154. When performing the shimming, therefore, after the static magnetic field in the imaging region has been measured, a process is repeated in which superconducting coil 112 is demagnetized, shim tray 152 is removed, the amount of magnetic material shims 154 is adjusted, shim tray 152 is inserted into superconducting coil 112, and superconducting coil 112 is demagnetized again. Here, the repeating of demagnetization and excitation of superconducting coil 112 not only results in large consumption of a freezing mixture such as liquid helium for keeping superconducting coil 112 in a superconducting state, but also may lead to quenching of superconducting coil 112. In static magnetic field adjustment device 150 for an MRI according to one embodiment, however, since the discrepancy between the calculated magnetic field output value and the actual magnetic field output value can be suppressed, the homogeneity of the static magnetic field in the imaging region is readily obtained with fewer adjustments of the amount of magnetic material shims 154 than conventional shimming. As a result, the number of times superconducting coil 112 is demagnetized and excited in the shimming can be reduced, whereby the large consumption of the freezing mixture and the quenching can be suppressed.

Further, in the present embodiment, as shown in FIG. 5, the sum of thickness d1 of magnetic material shims 154, thickness d2 of bottom spacer 157 and thickness d3 of top spacer 158 is substantially equal to depth d4 of shim pocket 153. In other words, shim pocket 153 is filled with magnetic material shims 154 and shim spacers 156. Accordingly, once shim pocket 153 is covered with cover 159, the movement of magnetic material shims 154, bottom spacer 157 and top spacer 158 in shim pocket 153 is suppressed. As a result, the discrepancy between the calculated magnetic field output value and the actual magnetic field output value can be suppressed.

Additionally, in the present embodiment, as shown in FIG. 5, thickness d2 of bottom spacer 157 and thickness d3 of top spacer 158 are substantially equal. Thus, bottom spacer 157 and top spacer 158 can share the same type of component. When calculating the magnetic field output value assuming, for example, that center C1 of magnetic material shims 154 does not coincide with center C2 of shim pocket 153, it is not necessary for thickness d2 of bottom spacer 157 and thickness d3 of top spacer 158 to be equal.

Second Embodiment

Figure 9:
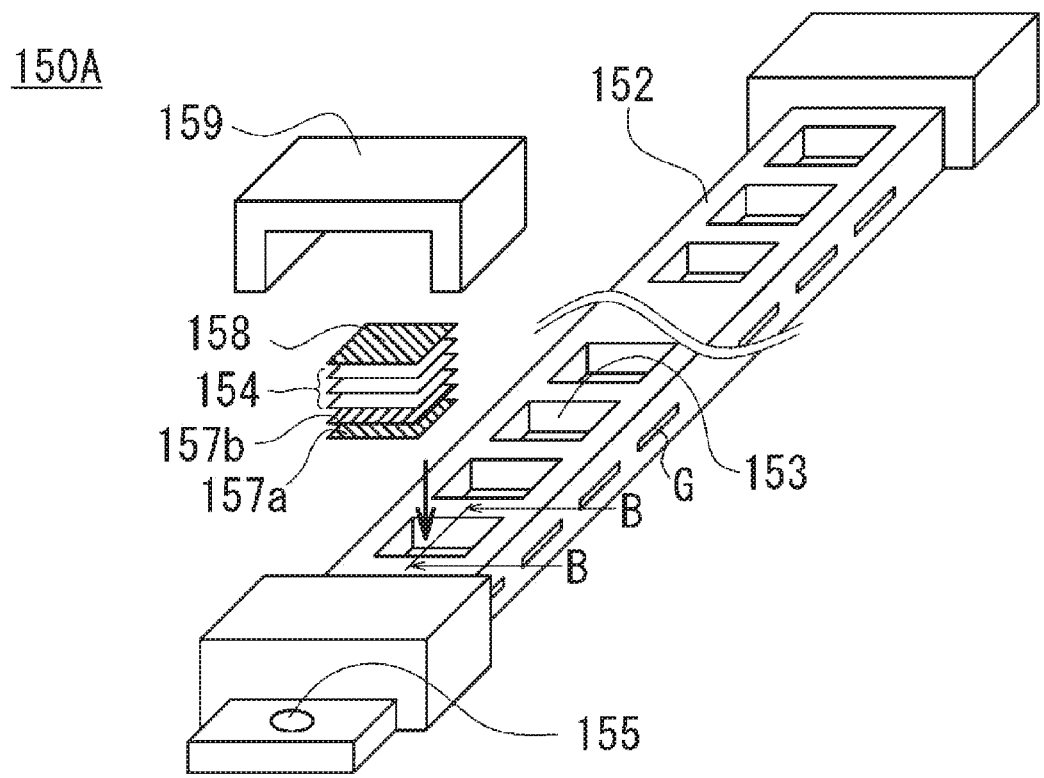
FIG. 9 is a perspective view of a static magnetic field adjustment device for an MRI according to a second embodiment.
Figure 10:
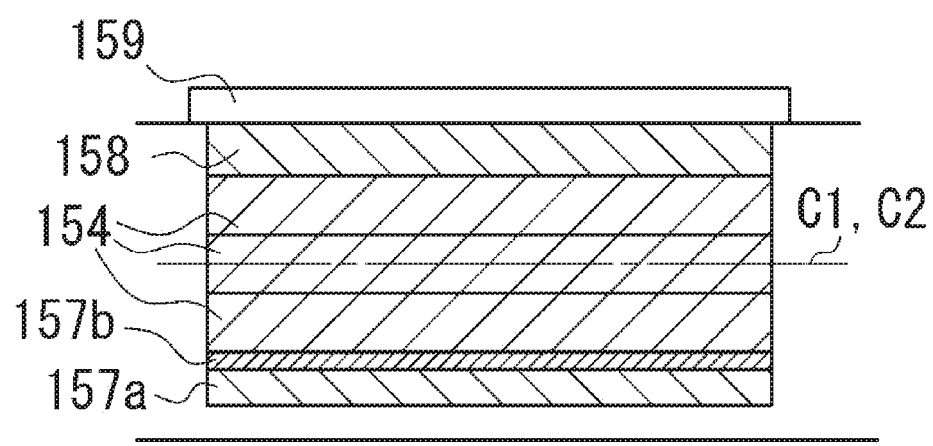
FIG. 10 is a sectional view taken along the line B-B in FIG. 9.

A main difference between a static magnetic field adjustment device 150A for an MRI according to a second embodiment and static magnetic field adjustment device 150 for an MRI according to the first embodiment is that bottom spacer 157 is formed of two components, namely, a bottom spacer 157a and a bottom spacer 157b, as shown in FIGS. 9 and 10. A specific description is given below.

Static magnetic field adjustment device 150A for an MR1 includes bottom spacer 157a made of Bakelite, and bottom spacer 157b made of PET. Bottom spacer 157b made of PET is thinner than bottom spacer 157a made of Bakelite.

Since bottom spacer 157 is formed of a plurality of components of different materials instead of a single component, the height of magnetic material shims 154 in shim pocket 153 can be more finely adjusted. For example, when disposing bottom spacer 157 in shim pocket 153, bottom spacer 157a made of Bakelite is first disposed in shim pocket 153 for simple adjustment of the height of magnetic material shims 154 in shim pocket 153, as shown in FIG. 10. Then, bottom spacer 157b made of PET can be disposed between magnetic material shims 154 and bottom spacer 157a, for fine adjustment of the height of magnetic material shims 154 in shim pocket 153.

The other features of static magnetic field adjustment device 150A for an MRI are similar to those of static magnetic field adjustment device 150 for an MR1. Therefore, the same description as that of static magnetic field adjustment device 150 for an MRI applies, except for the description of bottom spacer 157.

The features described in the embodiments above illustrate an example of the contents of the present invention, and can be combined with other known techniques, or can be partially omitted or changed within the scope not departing from the gist of the present invention.

REFERENCE SIGNS LIST

1 MRI (magnetic resonance imaging apparatus); 100 superconducting magnet; 150 static magnetic field adjustment device for an MRI; 152 shim tray; 153 shim pocket (recess); 154 magnetic material shim; 157 bottom spacer; 157a bottom spacer (first bottom spacer); 157b bottom spacer (second bottom spacer); 158 top spacer.

The invention claimed is:

1. A static magnetic field adjustment device for a magnetic resonance imaging apparatus, for adjusting a static magnetic field in an imaging region of the magnetic resonance imaging apparatus, the static magnetic field adjustment device comprising:
   a shim tray mounted on the magnetic resonance imaging apparatus and provided with a recess;
   a bottom spacer made of a non-magnetic material and accommodated in the recess to make contact with a bottom surface of the recess;
   a magnetic material shim made of a magnetic material and accommodated in the recess with the bottom spacer interposed between the magnetic material shim and the bottom surface; and
   a top spacer accommodated in the recess with the bottom spacer and the magnetic material shim interposed between the top spacer and the bottom surface,
   the recess being filled with the magnetic material shim, the bottom spacer and the top spacer, and
   the bottom spacer including a first bottom spacer and a second bottom spacer, a material of the first bottom spacer being different from a material of the second bottom spacer.

2. The static magnetic field adjustment device for a magnetic resonance imaging apparatus according to claim 1, wherein a sum of a thickness of the magnetic material shim, a thickness of the bottom spacer and a thickness of the top spacer is equal to a depth of the recess.

3. The static magnetic field adjustment device for a magnetic resonance imaging apparatus according to claim 2, wherein the thickness of the bottom spacer accommodated in the recess is equal to the thickness of the top spacer accommodated in the recess.

4. A superconducting magnet comprising the static magnetic field adjustment device for a magnetic resonance imaging apparatus according to claim 3.

5. A superconducting magnet comprising the static magnetic field adjustment device for a magnetic resonance imaging apparatus according to claim 2.

6. The static magnetic field adjustment device for a magnetic resonance imaging apparatus according to claim 1, wherein the thickness of the bottom spacer accommodated in the recess is equal to the thickness of the top spacer accommodated in the recess.

7. A superconducting magnet comprising the static magnetic field adjustment device for a magnetic resonance imaging apparatus according to claim 6.

8. A superconducting magnet comprising the static magnetic field adjustment device for a magnetic resonance imaging apparatus according to claim 1.

9. A static magnetic field adjustment device for a magnetic resonance imaging apparatus, for adjusting a static magnetic field in an imaging region of the magnetic resonance imaging apparatus, the static magnetic field adjustment device comprising:
   a shim tray mounted on the magnetic resonance imaging apparatus and provided with a recess;
   at least one spacer made of a non-magnetic material and accommodated in the recess, the at least one spacer including a bottom spacer that makes contact with a bottom surface of the recess;
   a magnetic material shim made of a magnetic material and accommodated in the recess with the bottom spacer interposed between the magnetic material shim and the bottom surface; and
   the recess being filled with the magnetic material shim and the at least one spacer,
   wherein
      the bottom spacer includes a first bottom spacer and a second bottom spacer, a thickness of the first bottom spacer being different from a thickness of the second bottom spacer.

10. The static magnetic field adjustment device for a magnetic resonance imaging apparatus according to claim 9, wherein
   the at least one spacer further comprises a top spacer accommodated in the recess with the bottom spacer and the magnetic material shim interposed between the top spacer and the bottom surface,
   a sum of a thickness of the magnetic material shim, a thickness of the bottom spacer and a thickness of the top spacer is equal to a depth of the recess provided in the shim tray.

* * * * *